United States Patent
Surcin et al.

[11] Patent Number: 5,896,982
[45] Date of Patent: Apr. 27, 1999

[54] SUPPORT PACKAGE FOR A SURGICAL SUTURE HAVING A STRAIGHT NEEDLE

[75] Inventors: Michel Surcin, Saint-Georges-sur-Eure; Martial Ohier, Breuillet, both of France

[73] Assignee: Ethnor, France

[21] Appl. No.: 09/057,253

[22] Filed: Apr. 8, 1998

[30] Foreign Application Priority Data

Apr. 18, 1997 [FR] France .................................. 97 04815

[51] Int. Cl.⁶ .................................................. A61B 17/06
[52] U.S. Cl. .......................................... 206/63.3; 206/784
[58] Field of Search .................................. 206/63.3, 380, 206/784, 525.1

[56] References Cited

U.S. PATENT DOCUMENTS

| | | | |
|---|---|---|---|
| 4,412,614 | 11/1983 | Ivanov et al. | 206/63.3 |
| 5,277,299 | 1/1994 | Holzwarth et al. | 206/63.3 |
| 5,555,976 | 9/1996 | Pernot | 206/63.3 |

*Primary Examiner*—Jacob K. Ackun

[57] ABSTRACT

The present invention relates to a support package (100) for surgical suture having a straight needle (20), the package being made by cutting out and folding a card blank comprising elements (110, 130, 160, 200) interconnected in pairs by fold lines (150, 180, 190), the support package being characterized in that a pair of holding elements (110, 200) is provided to sandwich the tip of the needle (20), a first element (200) of said pair including tongues (230, 240, 260, 270) for holding the needle and suitable, on either side thereof, for taking up position between corresponding cutouts (111, 112) in the second element (110) of said pair.

14 Claims, 4 Drawing Sheets

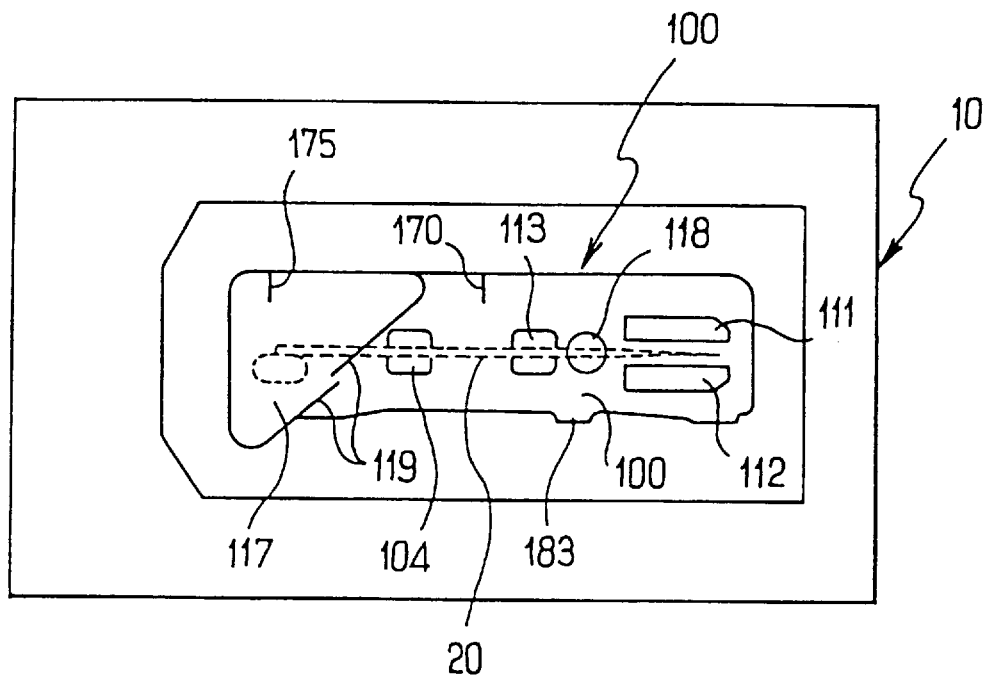
FIG_1
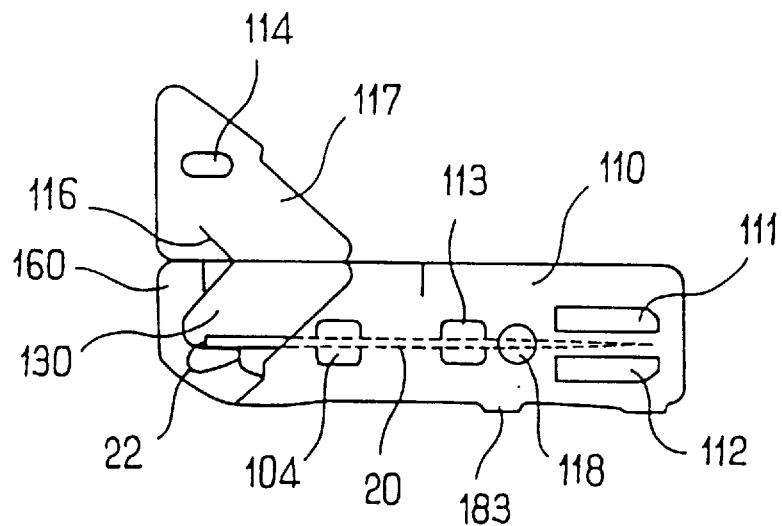
FIG_2

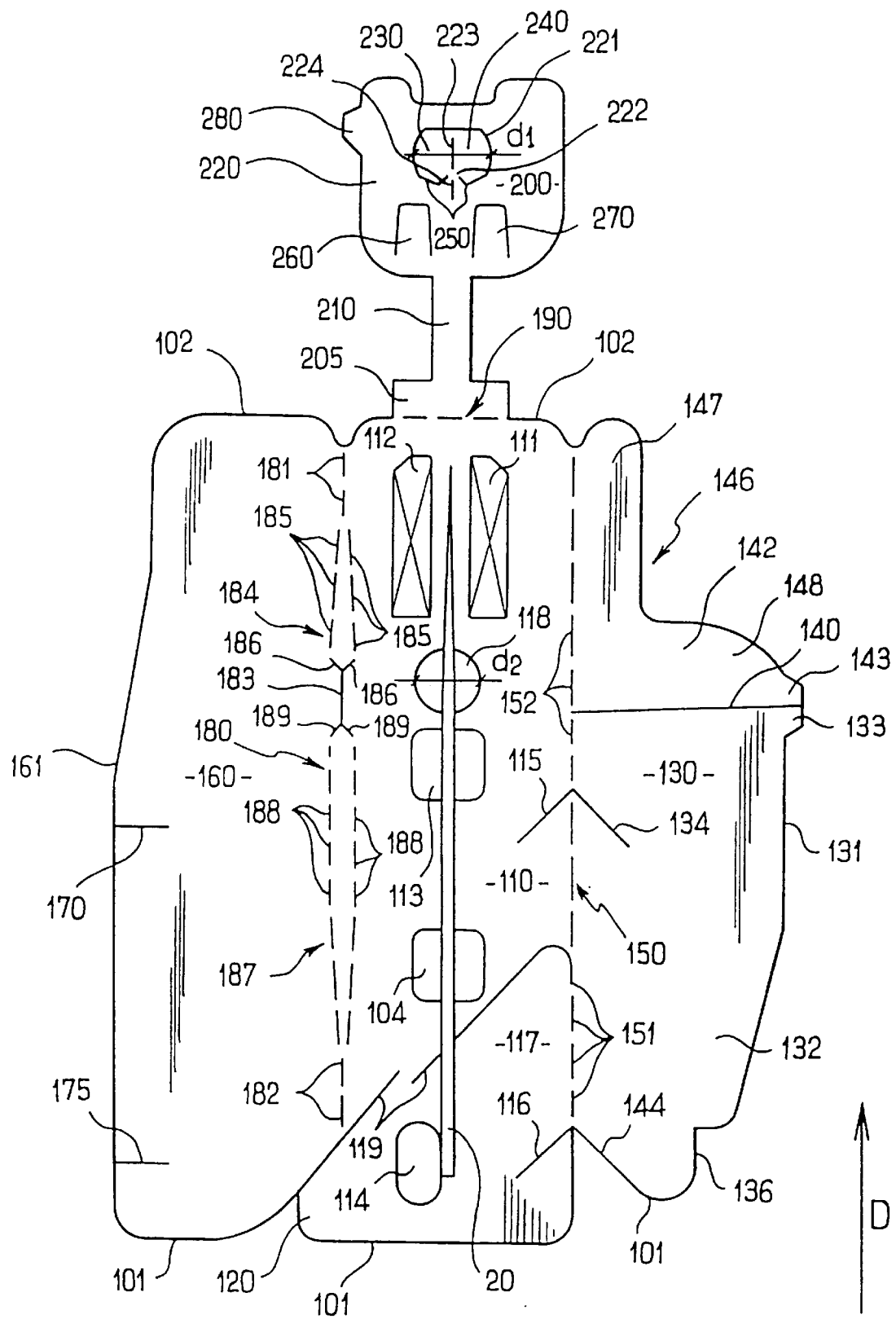
FIG_3

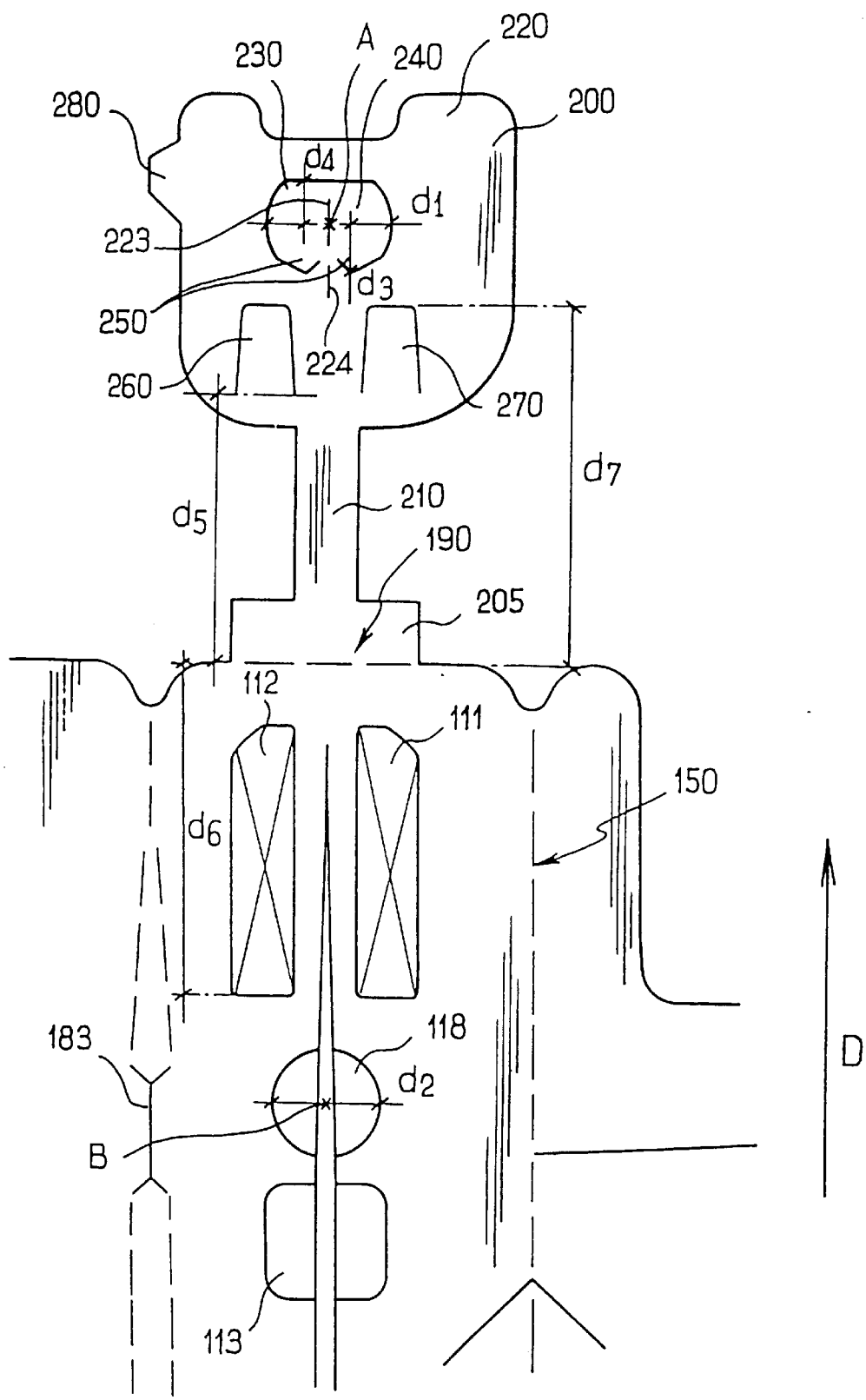
FIG_4

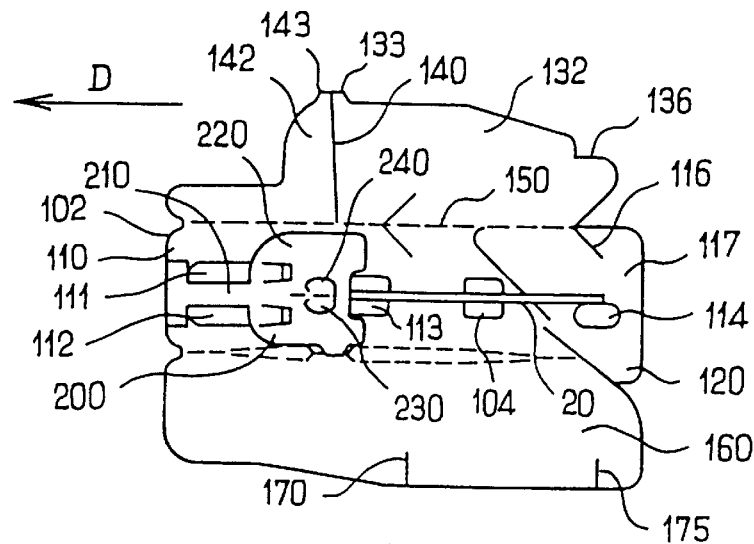
FIG_5a
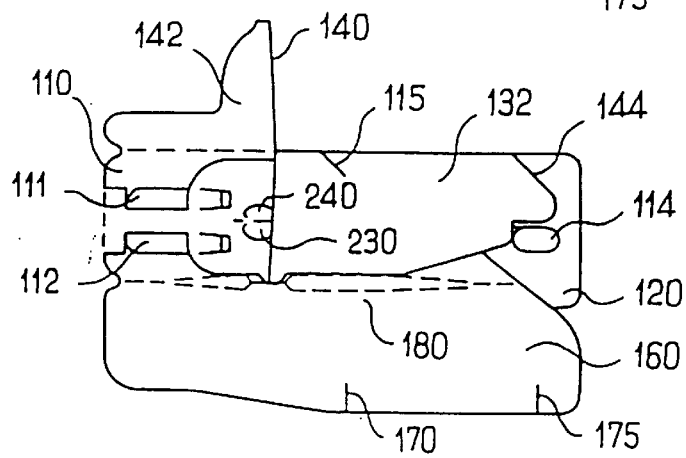
FIG_5b
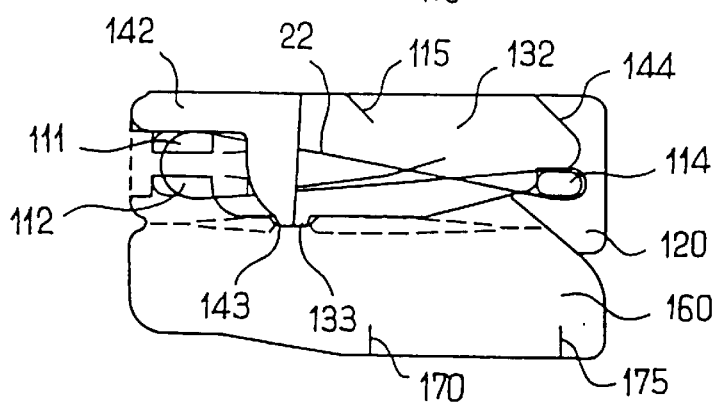
FIG_5c
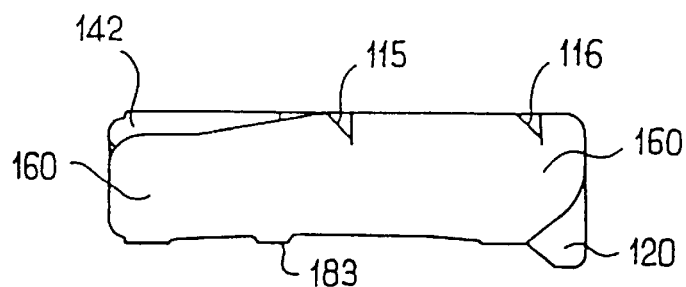
FIG_5d

SUPPORT PACKAGE FOR A SURGICAL SUTURE HAVING A STRAIGHT NEEDLE

The present invention relates to the field of surgical suture packaging.

Numerous kinds of packaging have already been proposed for surgical sutures.

For example, packaging has been proposed comprising a cradle of plastics material designed to be placed in a cardboard sheath prior to being inserted in a sterile outer envelope.

Packaging has also been proposed for a surgical suture each comprising a simple card package for placing inside a sterile envelope. Such a card package is commonly provided with at least one block of foam for receiving the tip of the needle.

An object of the present invention is to improve previously known packaging for a surgical suture.

In particular, a major object of the present invention is to propose novel surgical suture packaging designed to hold the tip of the needle firmly, both while the suture thread is being coiled, and also after the support package has been closed, and to do without making use of an additional block of foam, the novel packaging being particularly adapted for rectilinear needles.

In the context of the present invention, this object is achieved by a support package for a surgical suture having a straight needle, the package being made by cutting out and folding a card blank comprising elements separated by fold lines, in which a pair of holding elements is provided to sandwich the tip of the needle, a first element of said pair including tongues for holding the needle and suitable, on either side thereof, for taking up position under corresponding cutouts in the second element of said pair.

Other characteristics, objects, and advantages of the invention appear on reading the following detailed description given with reference to the accompanying drawings given by way of non-limiting example, and in which:

FIG. 1 is a diagrammatic plan view of packaging for a surgical suture in accordance with the present invention, shown in its closed and locked position;

FIG. 2 is a plan view of the support package of the present invention after a pivotally-hinged flap has been opened;

FIG. 3 is a plan view of a card blank used for implementing a support package of the present invention;

FIG. 4 is an enlarged view of the same card blank, showing its portion that has two holding elements of the invention;

FIG. 5a is a plan view of a card blank of the present invention on which a needle is disposed, and having a holding element folded down over the tip of the needle;

FIG. 5b shows a similar overall view in which a portion of an internal element of the present invention has been folded over the needle;

FIG. 5c shows the same overall view but further including suture thread after coiling, in which a second portion of an internal element of the present invention has been folded over the needle; and FIG. 5d shows the same overall view after all of the elements of the card blank have been folded over.

As can be seen in accompanying FIG. 1, the packaging for a surgical suture of the present invention essentially comprises a support package 100 placed in an outer envelope 10.

The outer envelope 10 is conventional and is therefore not described in greater detail below.

It is nevertheless recalled that this outer envelope 10 is sterile. It may advantageously be made up of two sheets suitable for peeling apart that are connected together via their margins to form a closed internal pocket suitable for containing the support package 100. By way of non-limiting example, the outer envelope 10 may be constituted by a first sheet based on paper and by a second sheet of an optically transparent plastics material.

In the accompanying drawings, the suture thread is given reference 22, while the needle is given reference 20.

The structure of the support package 100 of the present invention is described below.

The support package 100 is made by cutting and folding a single card blank, as shown in FIG. 3.

As can be seen from FIG. 3, the overall structure of the card blank is substantially elongate in a direction symbolized by arrow D and referred to below as the "main" direction of the card blank.

Four elements 110, 130, 160, and 200 are defined by folding. These four elements are held together in pairs by hinge lines 150, 180, and 190 which are described in greater detail below.

To simplify the following detailed description, the element 110 is referred to below as the "middle element", the element 130 as the "inner element" (because it is placed inside the package once it has been closed); the element 160 as the "outer element" because it is located on the outside of the package after it has been closed; and the element 200 as the "holding element" because it serves to hold the needle.

In addition, the terms "inner" and "outer" longitudinal edge are used respectively for the edges 131 and 161 of the blank as shown in FIG. 3, and the term "side" edges is used for the edges referenced 101 and 102 in FIG. 3. The end edges 101 and 102 are substantially orthogonal to the longitudinal edges 131, 161.

FIG. 3 corresponds to the inside face of the blank or package.

Fold line 150 which joins the middle element 110 to the inner element 130 is constituted by a series of cutouts 152 made up of disjoint rectilinear segments parallel to the longitudinal edges 131, 161. All of the segments 152 are in alignment.

The segments 152 thus extend substantially between the end edges 101 and 102.

The inner element 130 is perceptibly shorter than the element 110 in the direction of the fold lines 150 and 180, and its end adjacent to end edge 102 is more sharply rounded, the end of the line 150 adjacent to the end 101 being set back towards the inside of the card blank relative to the edge 101 of the middle element 110.

A second fold line 180 is formed between the middle element 110 and the outer element 160.

This fold line 180 is made up as follows:

two disjoint rectilinear cutout segments 181 that are in alignment and adjacent to the end edge 102;

two disjoint rectilinear cutout segments 182 that are in alignment with each other and that are in alignment with the segments 181, being adjacent to end edge 101;

a rectilinear central cutout segment 183 in alignment with the above-mentioned segments 181, 182; and two symmetrical sets 184 and 187 of cutouts, one set situated between the segments 181 and the central segment 183 and the other set between the segments 182 and the central segment 183.

Each of the two sets 184 and 187 comprises a pair of series of cutouts, referenced 185 and 188 respectively. Each series of cutouts 185 and 188 is made up of rectilinear segments in alignment. In addition, the two series of cutouts 185 and 188 in the sets 184 and 187 respectively diverge as they go towards the central segment 183.

Furthermore, each set of cutouts 184 and 187 has two additional segments 186 and 189 that constitute respective V-shapes. Thus, the additional segments 186 and 189 converge towards the central segment 183 and connect the ends of said central segment 183 respectively to the ends of the above-mentioned series of segments 185, 188.

The function of the fold line 180 formed in this way by the cutout segments 181 to 189 is to give volume to the support package 100. The person skilled in the art will easily understand that the thickness of the support package 100, after folding, will correspond to the spacing between the two series of cutout segments 185 and 188. In other words, the thickness of the support package increases progressively from the end edges 101, 102 towards the center of the package.

The structure of the middle element 110 is described below.

The middle element 110 includes a pair of through windows 111, 112 situated close to the edge 102. Each window 111 and 112 is generally rectangular in outline, with rounded corners. The windows 111 and 112 are elongate parallel to fold lines 150 and 180. The pair of windows 111 and 112 are disposed symmetrically about a midplane orthogonal to the elements 110 and parallel to the fold lines 150 and 180. This midplane coincides with the axis of the needle when it is mounted on the support package.

This midplane is referred to below as the "main" midplane.

The purpose of the windows 111 and 112 is to allow the pegs of temporary suture thread supports to pass through in conventional manner while the thread is being wound.

The element 110 also has a rear window 114 situated close to end edge 101. The outline of the window 114 is made up of two long parallel sides interconnected by two end semi-circles. The center of the window 114 is distant from the edges of the two through windows 111 and 112 which are adjacent to end edge 102, by a distance that is equivalent to the length of the needle 20. The window 114 is also offset laterally from the plane of symmetry between the windows 111 and 112.

In the assembled position, the tip of the needle is located between the two through windows 111 and 112, while the opposite end of the needle is adjacent to the window or passage 114 which has one of its sides flush with the needle, and extending beyond its end remote from the tip.

The rear window 114 is designed to receive a peg of complementary shape and which serves as a temporary support for the suture thread being coiled thereon.

Such a disposition for the window 114 having one of its long sides extending the needle 20 makes it possible to wind the suture thread 22 around the pegs without giving rise to a change in the direction of the thread 22 where it joins the needle 20.

The middle element 110 further includes a magnet passage 113 and a guidepiece passage 104 both of which are square in shape, being disposed on the main direction D of the card blank, between the through windows 111 and 112 and the passage 114. The magnet passage 113 and the guidepiece passage 104 are in alignment on the main direction D, each of them being symmetrical about the above-defined main midplane.

The passages 113 and 104 serve to pass respectively a needle-holding magnet and a needle-guidepiece during an initial stage of positioning the needle 20 on the card blank.

The magnet and the guidepiece may be of generally rectangular shape, having respective central grooves in their faces that come into contact with the needle. The magnet and the guidepiece also serve to position the shuttle on a moving reception tray of a machine for assembling the packages.

The middle element 110 also has a round orifice 118 whose center lies on the main midplane, between the windows 111, 112 and the passage 113, i.e. substantially one-third of the way along the middle element 110, starting from its edge 102. Compared with the reference position of the through windows 111 and 112, it is offset towards the inside of the middle element.

Adjacent to fold line 150, the middle element 110 further comprises two rectilinear cutouts 115 and 116. The cutouts 115 and 116 are at an angle relative to fold line 150, and advantageously at an angle of 45°, extending towards the edge 101 going towards the inside of the middle element 110. The cutouts 115 and 116 open out on the fold line 150 respectively halfway therealong and in the vicinity of the end thereof which is adjacent to the edge 101.

The middle element 110 also has a flap 117. The flap 117 includes a tab 120 adjacent to the end edge 101 and projecting beyond the fold line 180. Its purpose is to facilitate grasping the flap 117 so as to separate it in part from the middle element 110, as explained below.

The flap 117 is defined firstly by an staggered line formed by two cutout segments 119. The flap 117 is also hinged to the inner element 130 via a line constituted by various disjoint rectilinear cutout segments 151 that are in alignment, forming an integral portion of fold line 150. These segments 151 open out to the end edge 101.

The segments 119 which define the flap 117 thus connect the inner end of the line of-cutout segments 151 to the tab 120 in the vicinity of the end edge 101.

The structure of the holding elements 200 is described below. The element 200 is connected to the middle element 110 by a fold line 190 disposed on the end edge 102 of the middle element 110, towards which the tip of the needle 20 is directed when the needle is in its assembled position.

The element 200 is made up of three main portions: a rectangular portion 205, an oblong portion 210, and an enlarged square portion 220.

The portion 205 is a rectangle whose long side coincides with fold line 190, and whose other long side is connected in the middle to oblong element 210.

Element 210 is also rectangular and centered on the main midplane, extending along the main direction D. At its end remote from the element 205, the element 210 carries the element 220.

The element 220 is in the form of a square of width equal to the width of the middle element 110.

In a variant, the element 220 may be of any other shape, and is preferably enlarged perpendicularly to the direction D.

It will be observed that the length of the rectangular portion 210 is long enough for the square portion 220 to leave a major fraction of the windows 111 and 112 unobstructed after the holding element 200 has been folded onto the middle element 110. For the same reason, the width of the portion 210 corresponds to the width of the portion situated between the two windows 111 and 112.

Thus, as shown in FIG. 5a, after the holding elements 200 have been folded onto the middle element 110, the portion 210 overlies the zone extending between the windows 111 and 112 starting from the edge of the windows 111 and 112 that is adjacent to end edge 102, and extending approximately over two-thirds of the length of the windows 111 and 112. In this folded position, the square portion 220 covers one-third of the area of each window 111, 112, i.e. the third closer to the center of the card blank, and it extends towards the central portion of the card blank of the middle element 110, covering the round orifice 118 and extending to the edge of the magnet passage 113 which is closest to the round orifice 118.

In its central zone, the portion 220 has a cutout line 221 which is substantially elliptical in shape with its major axis perpendicular to the main direction D. Cutout line 221 is interrupted at the central portion 222 of one of the long sides of the elliptical shape. In this case, the long side faces the middle element 110, when the card blank is in its unfolded position. The cutout line 221 is thus a continuous line whose ends come close together in the vicinity of a junction 222 lying on the main midplane and on the side of the ellipse defined in this way that is closer to the middle element 110. The elliptical shape defined by the cutout 221 is symmetrical about the main midplane.

More precisely, the cutout 221 is constituted by a rectilinear cutout perpendicular to the main direction D and extended at both ends in the main direction D towards the middle element 110 by flanks that curve towards the inside of the portion 220, said flanks then coming close together, each forming a dihedral angle whose center extends in the main direction D, and which is open going away from the middle element 110.

A rectilinear cutout 223 is made inside the zone surrounded by the cutout 221 and on the main midplane. Another rectilinear cutout on the main midplane 224 is formed outside said zone which is adjacent to the junction zone 222.

The cutout 221 and the cutout 223 thus define two tongues 230 and 240 which extend perpendicularly to the main direction D and which have a common fold line embodied by the cutouts 223 and 224.

As can be seen in FIG. 3, each of the ends of the cutout 221 in the vicinity of the junction zone 222 constitutes one limb of a V-shape which is open towards the middle element 110. In this way, each of the tongues 230 and 240 has an extension 250 which extends towards the middle element 210 in the vicinity of the junction zone 222. In the preferred embodiment shown in FIG. 3, each of the extensions 250 has an outline in the form of a dihedral pointing towards the middle element 110.

The cutout 221 is disposed at a distance from the fold line 190 that is substantially equal to the distance between the orifice 118 and the line 190 such that the tongues 230 and 240 can be engaged in the orifice 118, on either side of the needle 20, after the element 200 has been folded onto the element 110.

More precisely, and as shown in FIG. 4, the center A of the set of two tongues 230 and 240 is at a distance from the fold line 190 that is equal to the distance between the center B of the orifice 118 and said fold line 190.

The distance d4 measured parallel to the line 150 between the center A and the outside edge of the pair of tongues 230, 240 is smaller than the radius of the orifice 118.

The distance d3 measured parallel to the line 150 between the center A and the ends of the extensions 250 is greater than the radius of the orifice 118.

The width d1 of the set of two tongues 230 and 240 taken parallel to the fold line 190 is greater than the diameter d2 of the orifice 118.

As can be seen in FIG. 3, the square portion 220 of the holding element 200 has a projecting tab 280 on its side which is parallel to the line 150 and looking towards the outer element 160. This tab 280 is designed to co-operate with the cutout 183 so as to lock closure of the element 200 on the middle element 110.

The square portion 220 also has two tongues 260 and 270 disposed on opposite sides of the main midplane, defined by U-shaped cutouts whose limbs point towards the middle element 110 and which therefore extend parallel to the main direction D.

As shown in FIG. 4, the distance d5 between the ends of the limbs of the U-shapes forming the tongues and the fold line 190 is slightly shorter than the distance d6 between the short edges inside the middle element 110 of the windows 111 and 112 and the fold line 190.

The distance d7 between the base segment of each of the U-shapes forming the tongues 260 and 270 and fold line 190 is slightly greater than the distance d6. Thus, after the holding element 200 has been folded onto the middle element 110, each of the tongues 260 and 270 is suitable for penetrating into a respective one of the windows 111 and 112 and taking up a position under the short edges of the windows 111 and 112 that are towards the inside of the middle element 110.

The structure of the inner element 130 is described below.

This inner element 130 is advantageously split into two portions 132 and 142 by a cutout 140.

The cutout 140 is advantageously rectilinear. It connects fold line 150 to the longitudinal edge 131. More precisely, the line of the cutout 140 is advantageously at an angle of about 80° relative to fold line 150.

The inner element 130 has two projections 133 and 143 which extend beyond a rectilinear central portion that is parallel to the main direction D of the edge 131, said projections being disposed on respective sides of the cutout 140, i.e. respectively on portion 132 and on portion 142.

The width of the inner element 130 taken parallel to the end edges 101 and 102 is equal to the corresponding width of the middle element 110, and the purpose of the two projections 133 and 143 is to penetrate into the above-mentioned central cutout 183 to enable the inner element 130 and the middle element 110 to be held together in a closed and adjacent position.

In addition, the inner element 130 includes, adjacent to fold line 150, a rectilinear cutout 134 which is symmetrical to the cutout 115 abut the axis of fold line 150. The cutout 134 is thus inclined at about 45° relative to the line 150, and its end adjacent to the line 150 coincides with the adjacent end of cutout line 115.

In similar manner, the outline of element 130 in its portion adjacent to the line 150 has a rectilinear portion 144 that is symmetrical to the cutout 116 about fold line 150. The junction point between the outline of element 130 and the line 150 thus coincides with the end of the cutout 116 which is adjacent to the line 150.

The cutouts 115 and 134 superpose when the inner element 130 is folded onto the middle element 110, and the same applies to the cutout 116 and the rectilinear edge 144. In this way, the pair of cutouts 115 and 134, and the pair comprising the cutout 116 and the rectilinear portion 144 constitute two lugs whose function is to co-operate with complementary cutouts 170 and 175 provided on the longitudinal edge 161 of the outer element 160 in order to lock the support package 100 in its closed position.

The first portion 132 of the inner element 130, adjacent to end edge 101 further includes a cutout 136 facing the window 114 formed through the middle element 110 to enable the portion 133 to be folded over the middle element 110 without said portion 132 interfering with the peg placed through the window 114. The cutout 136 is advantageously constituted by two rectilinear cutouts that meet at a right angle, one of the sides being parallel to the main direction D and the other perpendicular to the direction D. The outline of the cutout 136 is advantageously matched to a portion of the outline of the orifice 114, including at least the rectilinear portion of the window 114 facing the line 150, and the rounded portion of the opening 114 on the inside of the middle element 110. More precisely, the side of the cutout 136 which is parallel to the direction D coincides with the rectilinear portion of the cutout 114 facing the fold line 150, and the side of the cutout 136 that is perpendicular to the direction D is flush with the rounded portion of the window 114 that is located on the inside of the middle portion 110. In this way, after the inner element 130 has been folded onto the middle element 110, the inner element 130 covers the needle 20 in its portion adjacent to the suture thread. This end portion of the needle 120 is thus sandwiched between the middle element 110 and the inner element 130 to provide proper holding of the needle 20.

As will be understood on examining the accompanying figures, the cutout 136 also serves to define means for holding the thread in its zone adjacent to the needle 20, while allowing a certain amount of freedom to the thread when the package is opened.

Thus, as explained below, when assembling the support package, the inner element 130 is folded over the middle element 110 before the pegs placed in the windows 111, 112, and 114 are withdrawn The second portion 142 is provided with a large cutout 146 which connects end edge 102 to longitudinal edge 131. The portion 142 is thus L-shaped, having a longitudinally extending limb adjacent to fold line 150 and a transverse limb which, after the portion 142 has been folded over the middle element 110, extends across the middle element 110 towards the inside of the middle element 110 relative to the windows 111 and 112. More precisely, the edge of the inside transverse limb of the L is flush with the inside short edges of the windows 111 and 112.

The cutout 146 is placed in register with the windows 111 and 112 made through the middle element 110 so as to enable the portion 142 to be folded onto the middle element 110 without said portion 142 interfering with the pegs located in the windows 111 and 112.

The structure of the outer element 160 as shown in the accompanying figures is described below.

This outer element 160 has two rectilinear cutouts 170, 175 which open out into the longitudinal side edge 161. The cutouts 170 and 175 extend perpendicularly to said edge 161, respectively halfway along the edge 161 and at the end of the edge 161 that is adjacent to the end edge 101.

The cutouts 170 and 175 are advantageously located at the same levels along the edge 161 in the direction of the fold line 150 as the ends of the cutouts 115 and 116 located towards the inside of the middle element 110.

The purpose of the cutouts 170 and 175 is to receive the two triangular shapes defined by the cutouts 115 & 134 and the cutout 116 together with the rectilinear edge 144, in order to hold the package closed in its closed position.

It will be observed that the corners of the three elements 110, 130, 160, and 200 are preferably rounded.

To assemble the suture support package 100 of the present invention, the procedure is essentially as follows.

The blank 100 is presented on a conventional coiling machine while in the flat state and after the various structures described above have been cut out. The needle 20 is put into a packaging position in which the needle 20 lies on the main midplane and the tip of the needle is flush with the short edges of the windows 111 and 112 which are adjacent to end edge 102. The needle is held in this position by a magnet and by a guidepiece that pass through the middle element 110 respectively via the passage 113 and the passage 104. Thread support pegs are also positioned in the windows 111, 112, and 114.

As shown in FIG. 5a, after the holding element 200 has been folded about fold line 190 onto the tip of the needle 20, the tongues 230 and 240 are pushed by two fingers of a machine into the round orifice 118, thereby taking up positions on either side of the needle beneath the edges of the orifice 118. The tongues 230 and 240 extend beneath the edges of the orifice 118 not only in the direction parallel to fold line 190, but also via the extensions 250 in the direction of line 150. Because of these extensions 250, the zones of interaction between the tongues 230 and 240 and the edges of the orifice 118 are considerably enlarged.

In addition, the V-shape of these extensions serves to lock the square portion 220 against sliding over the middle portion 110 parallel to line 150.

The tongues 230 and 240 thus surround the tip of the needle 20 and lock it beneath the edges of the orifice 118, thereby exerting reaction against the needle which presses it against the middle element. The resistance to folding of each of the tongues 230 and 240 then opposes any movement of the needle perpendicularly to its axis.

As from this first step, the tip of the needle is prevented from moving sideways. The sandwiching of the needle held by mechanical reaction from the tongues 230 and 240 also opposes sliding of the needle along its own axis. The needle 20 is advantageously clamped by the tongues 230 and 240 in a zone that is close enough to its tip for the needle to be tapering or even conical in shape.

If the needle were to slide towards its tip, then the tongues 230 and 240 would be subjected to additional deformation, of a kind that is difficult to achieve without applying external force to the needle.

This retention against axial sliding is improved by folding down the other elements of the card blank onto the needle and onto the middle element 110.

Simultaneously, or in a second step, the tongues 260 and 270 are engaged in the windows 111 and 112 taking up a locking position beneath the edges of the windows 111 and 112 facing the orifice 118. In this case also, the tongues 260 and 270 are pushed into the windows 111 and 112, each by a finger under the control of said machine. The set of tongues 230, 240, 260, and 270 lock the holding element 200 against the middle element 110. The portion 200 is also locked in its folded position by inserting the projection 280 into the cutout 183.

As shown in FIG. 5b, the portion 132 is then folded onto the portion of the needle adjacent to the suture thread 22. At this stage, the needle is completely covered by the elements 132 and 200. Coiling is then performed in conventional manner on the above-mentioned pegs.

Coiling is advantageously performed in a figure-of-eight configuration to prevent any untimely tangling of the thread while it is in use.

After coiling, as shown in FIG. 5c, the portion 142 of the inner element 130 is folded onto the middle element 110 without interfering with the pegs passing through the windows 111 and 112. The structure thread 22 is thus properly held against the middle element 110 and the portion 142 of the inner element 130.

As shown in FIG. 5c, the portions 132 and 142 hold the thread where they join each other at 140. They thus act as a clamp closing onto the coil 22 in the tensioned state. This way of using the elements 132 and 142 is particularly effective in holding the thread in its coiled position. The pegs that were passed through the windows 111, 112, and 114 can then be retracted without the coil being subjected to excessive movement.

The portions 132 and 142 are locked onto the middle element 110 by inserting the respective projections 133 and 143 into the central cutout 183. The outer element 160 can then be folded down, as shown in FIG. 5d onto the inner element 130.

The outer element 160 is prevented from moving by the triangular-shape defined by the cutouts 115, 116, and 134, and the rectilinear margin 144 being engaged in the cutouts 170 and 175.

It will also be observed that in accordance with the invention, the suture thread 22 is situated essentially between the outer element 160 and the inner element 130, while the needle 20 is situated between the middle element 110 and the assembly comprising the inner element 130 and the holding element 200. In this way, the element 142 and the holding element 200 serve to keep the needle 20 separate from the thread 22, thereby avoiding any deterioration of the thread 22 in storage.

It then suffices to take hold of the handling tab 120 and to pull on the flap 117 by using the tab to make the previously disjoint segments 119 run into each other, thereby enabling the flap 117 to be pivoted about the hinge line defined by the segments 151, as can be seen in FIG. 2.

The practitioner can then easily take hold of the portion of the needle 20 which is adjacent to the suture thread 22 and extract the needle by a longitudinal sliding movement.

In the open position, the hinged flap 117 can serve as a prop enabling the support package to be held in a generally vertical position.

The support package of the present invention is particularly simple, reliable, easy to use, and effective in preventing any movement of the needle 20 prior to use.

Where appropriate, the support package 100 which is made of card can have printing on its outside face, e.g. for the purpose of identifying the nature of the thread 22 or of the needle 20, and the dimensions thereof.

For this purpose, the outer envelope 10 preferably includes at least one optically transparent sheet to enable the information printed on the support package 100 to be read before the envelope 10 is opened.

Naturally, the present invention is not limited to the particular embodiment described above but extends to any variant coming within the spirit of the invention.

Conversely, the lateral tongues 260 and 270 can be omitted, with the tongues having a common axis 230 and 240, and the orifice 118 sufficing on their own to hold the tip of the needle.

In particular, in a less complex version, the orifice 118 and the common axis tongues 230 and 240 may be omitted, and only the lateral tongues 260 and 270 used to hold the tip of the needle.

We claim:

1. A support package for a surgical suture having a straight needle, the package being made by cutting out and folding a card blank comprising four elements separated by three fold lines, the support package being characterized in that a pair of holding elements is provided to sandwich the tip of the needle, a first element of said pair including tongues for holding the needle and suitable, on either side thereof, for taking up position under corresponding cutouts in the second element of said pair.

2. A support package according to claim 1, characterized in that, two of said tongues have a common folding axis coinciding with the axis of the needle when said pair of elements is in the folded position.

3. A support package according to claim 2, characterized in that, said corresponding cutouts form a common orifice with the two tongues having a common fold axis taking up position beneath the edges thereof.

4. A support package according to claim 2, characterized in that the tongues, having the same fold axis, are made by a continuous cutout whose ends come close together at a junction point located on said common fold axis.

5. A support package according to claim 3, characterized in that the tongues, having the same fold axis, are made by a continuous cutout whose ends come close together at a junction point located on said common fold axis.

6. A support package according to claim 4, characterized in that each of the tongues, having the same fold axis, presents an additional extension extending along the fold axis beyond said junction point.

7. A support package according to claim 3, characterized in that, in the closed position of the support package, the tongues having the same fold axis extend beneath the edges of said single orifice firstly in a direction perpendicular to their fold line, and secondly in the direction of their fold line by means of their said additional extensions.

8. A support package according to claim 6, characterized in that, said single orifice is circular in shape.

9. A support package according to claim 1, characterized in that, one of the elements of said pair of holding elements has windows designed to pass pegs that serve as abutments for the suture thread while it is being coiled, and disposed on either side of the location for the needle, and in that the other element of the pair carries side tongues suitable for taking up position beneath one of the edges of each of said windows.

10. A support package according to claim 1, characterized in that, the holding tongues comprise tongues extending along the main direction of the location for the needle.

11. A support package according to claim 8, characterized in that, said other element of the pair includes a central portion whose dimensions are complementary to the dimensions of the zone extending between said windows designed for passing pegs, and suitable for covering said zone when the needle is sandwiched between the two holding elements.

12. A support package according to claim 8, characterized in that, said other element includes a central portion of oblong shape, having the same main axis as the location for the needle, and carrying at one of its ends a fold line delimiting the two elements of said pair of holding elements, and at its other end an enlarged portion carrying the holding tongues.

13. A support package according to claim 11, characterized in that, said other element includes a central portion of oblong shape, having the same main axis as the location for the needle, and carrying at one of its ends a fold line delimiting the two elements of said pair of holding elements, and at its other end an enlarged portion carrying the holding tongues.

14. A support package according to claim 1, characterized in that one of the elements of the pair of holding elements carries at least one projecting tooth designed to penetrate in a complementary cutout in order to lock the pair of elements together one against the other.

* * * * *